United States Patent [19]

Whelchel et al.

[11] Patent Number: 4,612,872
[45] Date of Patent: Sep. 23, 1986

[54] METHOD OF OPERATING AN EXPANDABLE CHAMBER WITH DELAY VALVE

[75] Inventors: Robert C. Whelchel, Newport Beach, Calif.; Roger S. Sanderson, 24662 Santa Clara, Dana Point, Calif. 92629

[73] Assignee: Roger S. Sanderson, Dana Point, Calif.

[21] Appl. No.: 512,151

[22] Filed: Jul. 8, 1983

[51] Int. Cl.⁴ .................... G01K 11/08; G01K 5/34
[52] U.S. Cl. .................................. 116/218; 422/26; 422/28; 422/38; 422/116; 422/295; 422/310; 137/468; 116/220
[58] Field of Search ............... 137/468; 422/116, 226, 422/26, 38, 295, 310, 28; 116/220, 218

[56] References Cited

U.S. PATENT DOCUMENTS

| | | |
|---|---|---|
| 2,092,445 | 9/1937 | Doulgheridis . |
| 2,997,397 | 8/1961 | Doulgheridis . |
| 3,904,111 | 9/1975 | Peterson ............................. 137/468 |
| 4,149,650 | 4/1979 | Sanderson . |
| 4,190,987 | 3/1980 | Naidus ............................. 52/232 |
| 4,196,166 | 4/1980 | Sanderson . |
| 4,228,914 | 10/1980 | Sanderson . |
| 4,247,517 | 1/1981 | Sanderson . |
| 4,251,482 | 2/1981 | Sanderson . |
| 4,318,070 | 3/1982 | Dohrmann et al. ............... 337/13 |
| 4,335,071 | 6/1982 | Thornton ......................... 422/116 |
| 4,372,921 | 2/1983 | Sanderson . |
| 4,374,570 | 2/1933 | Sanderson . |
| 4,416,417 | 11/1983 | Sanderson et al. ............. 236/92 R |
| 4,457,327 | 7/1984 | Pepper ............................ 422/310 |

Primary Examiner—David L. Lacey
Assistant Examiner—Titus B. Ledbetter, Jr.
Attorney, Agent, or Firm—Knobbe, Martens, Olson & Bear

[57] ABSTRACT

A method of operating an expandable chamber formed with a valve opening in a wall of the chamber, which permits the surrounding environment, such as high temperature steam, to enter the chamber is used. A temperature responsive delay valve closes the chamber to capture a quantity of the steam in an autoclave sterilizing cycle. The closing of the valve is delayed until the high temperature steam has been applied for a predetermined time. A later reduction in pressure surrounding the chamber causes the chamber to expand, which provides an indication that an adequate sterilizing cycle has been provided. The expansion force may also be used to permit a container to close at the end of a sterilizing cycle.

6 Claims, 6 Drawing Figures

METHOD OF OPERATING AN EXPANDABLE CHAMBER WITH DELAY VALVE

BACKGROUND OF THE INVENTION

This invention relates primarily to the sterilizing of medical items such as instruments and linens utilized in hospital's or doctor's offices. The invention is more particularly directed to an article of manufacture that can serve as an indicating device that will provide a positive indication that a proper sterilizing cycle has been provided by an autoclave. The device is also useful as a mechanical actuator responsive to a sterilizing cycle.

U.S. Pat. Nos. 4,247,517, 4,251,482, 4,374,570 and 4,372,921 disclose systems for storing medical items while they are being sterilized, stored, used, and awaiting resterilization. These systems utilize a container that is automatically closed within an autoclave near the completion of a sterilizing cycle so that the articles being sterilized are sealed within a vacuumized container when the container is removed from the autoclave, thus guaranteeing sterility. The primary means employed to obtain the automatic closing of the container is an expandable chamber which captures a quantity of the sterilizing steam utilizing a temperature responsive valve means. The captured steam later causes the chamber to expand and the expansion force is utilized to close or to permit the container to close. The valve closing the chamber is responsive to the steam temperature. Thus it captures the steam fairly early within a sterilizing cycle. It is important however that the chamber not expand to provide an actuating force until near the end of the sterilizing cycle so that steam remains in contact with the container contents during the entire steam phase of the cycle.

It has been found that some malfunctioning have significant pressure variations during the high pressure steam phase of the sterilizing cycle. These pressure variations can cause the expandable chamber to expand sooner than desired with the result that the container contents would not be in contact with further steam entering the autoclave and therefore may not be adequately sterilized.

The problem has been greatly compounded by the recent introduction of a different form of autoclave cycle. Earlier autoclaves provided only a single high pressure steam phase. While as indicated above, the pressure might vary somewhat during such phases, there was at least only one such phase. Recently however there have been introduced autoclaves that employ at the beginning of the cycle several pulses of high pressure steam followed by a short application of pressure reduction to hasten the removal of air and the steam. These bursts of steam might cause the temperature responsive valve means to close the expandable chamber actuator referred to above to capture a quantity of steam, and with the subsequent reduction of pressure would cause the closed chamber to expand thus providing a premature actuating force which would result in the container being closed before the contents have been subjected to the main application of high pressure steam. Accordingly, a need exists for a means to avoid this problem.

In the operation of an autoclave, a related problem which arises is that of knowing whether the autoclave has properly functioned so that there is an assurance that the articles when removed from the autoclave have been properly sterilized. For example, to provide proper sterilization by steam, it is necessary that steam of a certain temperature, pressure and saturation be applied for a certain period of time. An inadequate temperature will not adequately kill the bacteria. With steam of a pressure below a certain level, it is necessary that the temperature be higher or that the steam be applied for a longer period of time. For example, to put this in extreme, dry heat without steam requires a higher temperature for a longer period of time to provide sterilization than does lower temperature high pressure steam.

The current requirement is that steam at 270° F., 97% saturation and 30 psi be applied for at least three minutes. Chemical indicators are employed to attempt to provide assurance as to the adequacy of the sterilizing cycle. However, most of these indicators are primarily temperature responsive. That is, they will give an indication that the environment within the autoclave reached a certain temperature level. However, they do not give an adequate indication as to the length of time that the sterilizing environment was applied, nor do they give an indication that steam was present. Recently chemical indicators have been developed to indicate a minimum time the temperature was at a set level, but even these indicators can be turned by dry heat, and thus do not indicate that steam was present. These indicators employ a crystal that liquefies at a certain temperature and then travels through a wick to measure time.

In addition to providing steam, some autoclaves are separately heated. Thus, this supplementary heating could cause an indicator to suggest that adequate sterilization was obtained when the steaming capability of the autoclave may have malfunctioned or a burst of steam striking the indicator could affect the indicator.

Accordingly, a need exists for an improved indicator that will reliably tell whether a sterilizing cycle has been adequate. In addition to being reliable, such indicators must also be relatively inexpensive to be practical.

SUMMARY OF THE INVENTION

In accordance with this invention, there is provided an expandable chamber of the type referred to above, but added to this construction is a temperature responsive delay element which prevents the chamber from capturing a quantity of steam until the steam has been applied at a predetermined minimum temperature for a predetermined time. Thus, the actuator is not triggered to be operable until after adequate sterilizing steam has been employed.

Such an expandable chamber employing the temperature responsive delay means also results in a device that provides an indication that the proper sterilizing cycle has occurred. That is, if the expandable chamber is placed into the container before it is inserted into the autoclave, the chamber will not close to capture a quantity of steam until the steam has been applied for the necessary period of time at the necessary temperature to cause the temperature responsive delay element to permit the chamber to close. Further, if steam of an adequate pressure was utilized, the chamber will expand at the end of the pressurized phase of the steaming cycle. Thus when the container is removed from the autoclave, it is easy to see whether the expandable chamber indicator is in its expanded condition. If it is, this is an indication that a sterilizing cycle was adequate. Conversely an uninflated chamber means that the sterilizing cycle was not adequate and that the container should be resterilized.

In a preferred form of the invention, the inflatable chamber has a wall of stiff plastic that includes a projection that extends inwardly into the chamber. A valve opening in the wall of the projection places the interior of the chamber in communication with a passage in the projection leading to the exterior chamber. A valve member, preferably in the form of a sleeve surrounds this projection to close the valve opening at a predetermined temperature. A delay element, preferably in the form of a tubular sleeve is positioned between the valve member and projection, and this element is made of a material which is initially rigid to prevent the valve member from closing the valve opening, but the material will soften after being subjected to a predetermined temperature for a predetermined period of time and thus permit the valve member to press the softened delay element against the valve opening to close the valve and capture a quantity of steam within the chamber. The subsequent expansion of the chamber caused by a reduction of the surrounding pressure provides either an expansion force useful as an actuator or provides an indication that a proper sterilizing cycle has been applied.

DESCRIPTION OF THE PREFERRED EMBODIMENT

Figure 1:
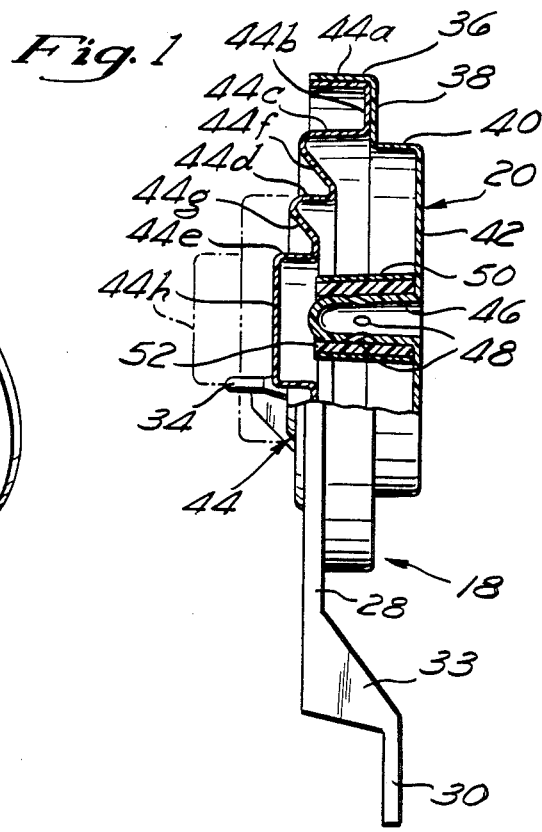
FIG. 1 is a cross sectional view of an expandable chamber illustrating the invention.
Figure 2:
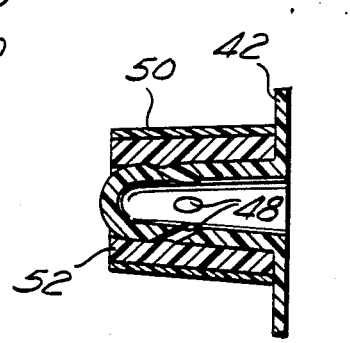
FIG. 2 is a enlarged cross sectional view of a portion of the structure of FIG. 1 showing the valve in a closed position.

Referring now to FIGS. 1 and 2, there is shown an actuator 18 including a plate-like member 28 having on its lower end a tab 30 which is useful for mounting the actuator in an area in which the force is desired. More specifically, the tab 30 is designed to be inserted in a slot of the base of a container used for sterilizing medical items. The container is not shown herein but is fully described in U.S. Pat. No. 4,372,921. The plate has generally a thin configuration, but is provided with a plurality of gussets 33 for strengthening the structure.

The upper portion of the plate 22 is molded with a circular cup-shaped recess of two different diameters. The outer portion includes a cylindrical wall 36, and an annular wall 38, which is further connected to a smaller diameter cylindrical wall 40 which is joined to a circular end wall 42.

This recess together with a separate bellows-like element 44 forms an expandable chamber 20. The support plate 28 should be sufficiently stiff and strong to support the lid of a container and to provide the necessary structural reliability. In addition, it should be relatively inexpensive so that it may be disposable. Molding support plate 28 in a single operation with multiple functions greatly contributes to this. Thus, the plate is preferably formed of a moldable, relatively inexpensive plastic. The bellows-like element 44 is preferably likewise molded of a plastic material similar to that from which the plate 28 is molded, but the element 44 is of a thinner cross section and is more flexible, thus being in a nature of a diaphragm. As can be seen, the diaphragm 44 includes an outer cylindrical wall 44(a) connected to an annular wall 44(b) which mates with the walls 36 and 38 on the plate 28. These walls are joined by suitable means to form expandable chamber 20. The diaphragm 44 further includes short cylindrical wall sections 44(c), 44(d) and 44(e) with consecutively smaller diameters joined by connecting wall sections 44(f) and 44(g). A central circular wall section 44(h) connected to the cylindrical wall 44(e) forms a nose or end wall of the chamber. As can be seen from the phantom lines in FIG. 1, the diaphragm 44 assumes the position indicated when the chamber is fully expanded. Note that the cylindrical walls maintain their approximate configuration but are moved outwardly due to the flexibility of the connecting annular wall sections 44(f) and 44(g).

The support plate 28 also includes a tubular projection or nipple 46 which is formed integral with the wall 42 and projects into the chamber 20. The inner end of the projection is closed but a plurality of ports 48 in the side wall of the projection connect the chamber to the interior passage of the projection leading to the exterior space around the chamber. The projection 46 tapers slightly inwardly to facilitate a single molding operation for the plate 28. Also, the ports 48 are formed at an angle to the side wall of the projection so that the ports may also be made during the molding operation. That is, the molding structure forming the interior of the projection and the ports may be withdrawn from the backside of the plate 28 at the completion of a molding operation. The material forming the plate is somewhat flexible to permit such action.

Positioned loosely over the projection 46 is a cylindrical sleeve 50 preferably made of heat-shrinkable material. Although the sleeve is relatively confined within the chamber, it may be more positively secured to the plate 42 by a small amount of adhesive under the sleeve.

In accordance with the invention, there is positioned a delay element in the form of a sleeve 52 which also surrounds the projection 46 but is located between the sleeve 50 and the projection. This delay element 52 is made of a heat responsive thermal plastic material which is relatively stiff at room temperatures but will soften at a predetermined elevated temperature, if it is subjected to that heat for a predetermined period of time. The inner diameter of the delay sleeve 52 is initially larger than the outer diameter of the projection 46, at least in the area of the ports or openings 48. Thus, even if the sleeve should happen to be positioned closely to one port 48, the opposite side of the sleeve would be spaced from the port on the opposite side of the projection. This is advantageous in that the parts can be fabricated without strict dimensional tolerances and can be easily assembled. The delay sleeve 52 and the valve sleeve 50 are positioned on the projection before the diaphragm 44 is secured to the plate 28. On each side of the chamber 20 there is positioned a post 34, one of which is shown in FIG. 1. These posts are formed integral with the plate during the one step molding operation of the plate. The posts are located with respect to the lower end of the plate to support the lid of a container, as described in U.S. Pat. No. 4,327,921.

Figure 5:
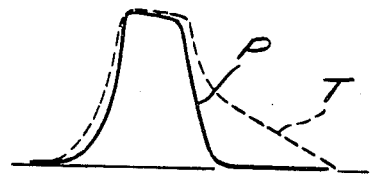
FIG. 5 is a graph of a gravity type autoclave cycle.

FIG. 5 illustrates an indicator 60 that is essentially like the structure of FIGS. 1 and 2 except that is only the inflatable chamber 20. Also, it is of smaller dimension in that it does not have to provide an actuating force, needing instead only enough volume in the collapsed condition to capture the necessary quantity of steam to cause the chamber to expand with a surrounding pressure reduction.

OPERATION

As mentioned above, one of the uses of the device known in FIG. 1 is that of an actuator which will provide an actuating force at a desired point. The device is particularly useful in connection with controlling the closing of a container used for holding items to be sterilized such as medical items. Thus, as more fully described in U.S. Pat. No. 4,372,921, a quantity of items to be sterilized, such as surgical instruments, are placed in the container and the container is placed in an autoclave with the actuator 18 holding the container lid open. That is, the tab 30 on the lower end of the actuator positioned in a slot in the base of the container, and the plate extends upwardly as illustrated in FIG. 1 with the posts 34 extending outwardly to receive the lower edge of the container lid and hold the lid in open position. Keep in mind that the expandable chamber will be in the solid position shown in FIG. 1 so that the diaphragm 44 does not extend out as far as the posts 34. Thus, there is room for the container lid to be supported on the post.

Figure 3:
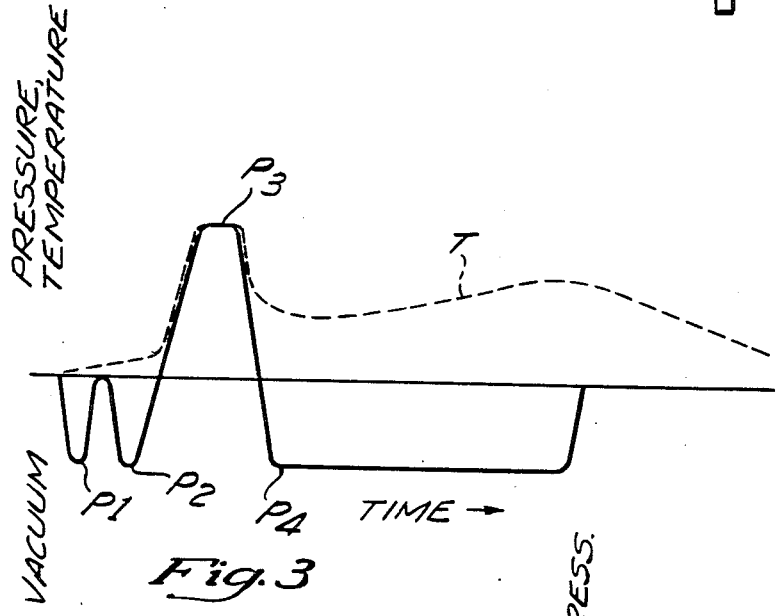
FIG. 3 is a graph illustrating the temperature and pressure conditions of a so called vacuum autoclave cycle.

There are a variety of autoclave cycles. FIG. 3 graphically illustrates the pressure and temperature conditions in one common type of autoclave cycle used in a so-called vacuum autoclave. In that cycle, the space within the autoclave is first subjected to two or more short preliminary vacuum phases to withdraw unsterile air from the containers. Thus, the pressure drops from atmospheric pressure to a lower level as indicated by the points P1 and P2, on the pressure line P in FIG. 3. The temperature line T starts to rise slightly during this period due to the heating typically applied around the autoclave enclosure. This temperature is not sufficient to affect either the valve member 50 or the delay element 52 and thus the pressure changes within the autoclave are felt on the interior of the inflatable chamber 20 because of the ports 48 in the same manner as felt on the exterior of the chamber. Consequently, the inflatable chamber does not expand at this time. Any pressure changes in the autoclave will automatically be applied to the interior of the chamber as well.

The autoclave then provides a sterilizing environment of high pressure steam for the desired period of time to sterilize the container. The sterilizing environment applied to the container will of course also enter the chamber 20 through the ports 48. The elevated temperature of the fluid will cause the sleeve-like valve member 50 to soften and shrink in a direction to cover the ports 48, thus providing a valve closing force which prevents flow out of the chamber. If the steam phase stayed in a small pressure range, it would be satisfactory for the chamber to close at that point and capture a quantity of steam within the chamber. However, it has been found that many autoclaves do not maintain very constant pressure during the steam phase. Instead there is often a series of steam injections which produce pressure rises, followed by a gradual decay of pressure. Such pressure drops if large enough could start to cause the expandable chamber to expand in view of the fact that higher pressure steam is captured in the interior. This would cause the container lid being supported by the post 34 to be prematurely released.

Due to the presence of the delay element 52, the compressive force from member 50 cannot immediately close the valve when the high temperature steam is applied. Instead the delay element delays the capturing of steam in the chamber and maintains the valve open until the steam has been applied for a certain period of time. That is, the delay element 52, being made of temperature responsive material, will not soften after it has been subjected to a certain minimum temperature for a period of time. This softening point is selected to be near the end of the steam phase P3. Once the element 52 softens, the compressive force of the valve member 50 urges the delay element inwardly against the valve ports 48 as shown in FIG. 2, thus capturing a quantity of the high pressure steam within the chamber.

At the completion of the steaming phase of the cycle, there is an immediate pressure drop due to the final vacuum which is applied to withdraw steam from the container, as indicated at P4 on the pressure line in FIG. 3. The temperature also drops but this is much more slowly. As the pressure drops in the autoclave, the expandable chamber starts to expand due to the fact that the pressure of steam captured within the chamber is greater than the pressure surrounding it. Thus, the bellows-like diaphragm 44 of the chamber 20 will move to the configuration shown in phantom lines in FIG. 1. Since the nose 44(h) of the diaphragm 44 is engaging the outer edge of the lid, the actuator plate is urged to pivot in a counterclockwise direction about its lower tab 30. The actuator moves because resistance to movement provided by the cantilever mounting arrangement for the plate is much less than that of the weight of the lid. Thus, as the actuator moves, its posts 34 are withdrawn from beneath the lid, allowing it to fall to a close position. The container is thus closed at the end of the sterilizing cycle such that the container is hermetically sealed before it is subjected to unsterilized environment.

If the container had been prematurely closed, its contents would not have been sterilized since the temperature of the steam is not sufficient to keep the interior of the container hot enough for a given period of time to adequately sterilize. That is, it is necessary that the steam circulate intimately with the material in the container. Also, premature closing of the container would capture steam and condensation within the container, which is undesirable.

In addition to being suitable to perform the basic functions, there are a number of advantages to the sleeve-like element 52. The element is simple, reliable and inexpensive. The material may be purchased in tubular lengths and then simply cut to the desired length. The softening point may be varied by either varying the composition of the material or by varying the thickness of the sleeve wall. While great precision is not necessary, it has been found that a desired softening point can be maintained quite precisely.

Figure 4:
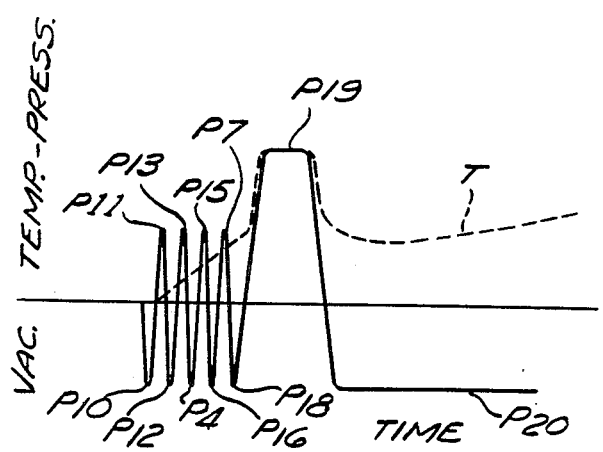
FIG. 4 is a graph indicating the temperature and pressure conditions of a so called pulser autoclave cycle.

As mentioned above, some autoclaves now provide short bursts of steam at the beginning of a cycle. Such a cycle is indicated in FIG. 4 wherein there is first provided a preliminary vacuum indicated at P10 followed by bursts of steam indicated by P11, P13, P15 and P17 which are followed respectfully by short vacuum phases P12, P14, P16 and P18. The temperature curve T is shown gradually increasing at that point in that the steam bursts do not immediately raise the temperature of the autoclave interior to the steam temperature. However, the steam is introduced into the autoclave interior as jets from a nozzle. Thus, if an inflatable chamber 20 of an actuator 18 happened to be situated in the autoclave in the path of the steam jet, a heat-shrinkable valve member 50 without the delay element 52, could cause the chamber valve ports 48 to close capturing a pressurized atmosphere within the chamber. The reduction pressure occurring immediately after the bursts of steam would cause the inflatable chamber to expand and release the container lid prematurely such that the container contents would not be sterilized.

The delay element however avoids this problem in that the bursts of steam even if striking the inflatable chamber would not be of long enough duration to provide enough heat to cause the delay element to soften. Consequently, the chamber would not be closed. Instead, the chamber would remain open until the high-pressure steam phase T19 had been applied for the desired period of time to ensure sterility.

The actuator will properly function with other autoclave cycles too, such as the so called "gravity" cycle of FIG. 5, wherein there are no vacuum phases. The inflatable chamber would be closed near the end of the steam phase, and the subsequent reduction of pressure which occurs when the steam phase is ended will provide sufficient pressure drop to cause the chamber to expand and release the container lid. While utilizing the delay element is not mandatory, it will prevent an early pressure reduction in a malfunctioning autoclave from causing a container to close too soon.

Figure 6:
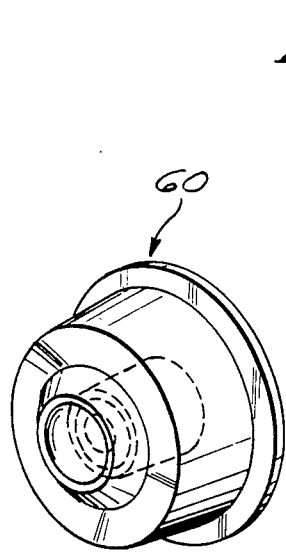
FIG. 6 is a perspective view of an expandable chamber similar to that of FIG. 1 but modified for use as an indicator.

The lightweight inflatable chamber indicator 60 of FIG. 6 functions in the same manner as described for the actuator of FIG. 1, but it does not, of course, function as an actuator. Instead it merely expands automatically at the appropriate point to indicate that a proper sterilizing cycle was obtained.

Although an actuator of the type shown in FIG. 1 provides an indication that a proper sterilizing cycle is obtained, it is necessary to utilize a separate indicator such as the type shown in FIG. 6 that is actually in the container in contact with the container contents. Also, the inflated indicator thus remains with the container to be observed at any time through the transparent cover of the container so as to tell the observer that the contents of the container was sterilized.

Standards now require that an indicator must be used in connection with any autoclave regardless of the type of packaging employed. It is necessary to check autoclave effectiveness to know that sterilizing cycles are adequate. Since indicators are so inexpensive, it is practical to include one in all packages.

In addition to a number of different types of sterilizing cycles as suggested by the graphs of FIGS. 3, 4 and 5, the steaming phase of a particular type of cycle is varied for different sterilizing applications. For example, to sterilize certain loads it may be necessary to apply the steam for five minutes, whereas for other loads it may be necessary to apply the steam for ten minutes or longer. The variance in time is to insure that the entire load is exposed to steam at 97% saturation and 270° F. temperature and 30 pounds of pressure. A single type of indicator is sufficient for this purpose, but the delay period for the actuator may be varied. This may be done by changing the wall thickness of the delay element 52 or changing the composition of the material to vary the length of time that it takes the delay element to soften after it is subjected to a predetermined minimum temperature. Thus, actuators of varying steam phase times may be stocked and selectively utilized as needed.

As one example, the delay element may be made of acrylic, which will begin to soften at a temperature of 250° F. With a sleeve wall thickness of about ⅛ inch, the element will soften to permit the valve to close after the temperature has been maintained for about five minutes. With a wall thickness of ⅜ inch, the sleeve will soften after about ten minutes.

What is claimed is:

1. A method of providing an indication of whether a steam phase of a sterilizing cycle in a sterilizer has been adequate to sterilize articles, comprising:

placing in an enclosed area to be sterilized, an indicator comprising an expandable chamber having means in a wall, forming a valve port, said valve port being open when the chamber is placed in said area;

applying pressurized steam to said area causing steam to enter the port thus applying steam to the expandable chamber;

providing means applying a valve closing force to an element for closing said port to capture a quantity of said steam in the chamber;

said element being constructed and arranged so as to delay the closing of said port and the capture of steam until steam of a predetermined temperature has been applied to the expandable chamber for a predetermined period of time sufficient to sterilize articles placed in said area; and allowing the pressure around the chamber to reduce to ambient pressure relative to the chamber pressure so that the captured steam will cause the chamber to expand thus indicating that pressurized steam of a predetermined temperature was applied for said sufficient time.

2. The method of claim 1 wherein said means applying the valve closing force is a resilient element and wherein said delay element is a rigid temperature responsive delay element positioned so as to prevent the resilient element from closing the port until the delay element has softened.

3. The method of claim 1 wherein said means in the wall is a tubular projection, and said means applying a valve closing force is a tubular valve element surrounding the projection, and said delay element is a rigid tubular sleeve positioned around said projection between the projection and the valve element, said delay element being temperature responsive so that it will soften after being subjected to said predetermined temperature for said predetermined time and then permit the valve element to force the delay element to cover said port.

4. The method of claim 1 wherein the period of time is at least three minutes.

5. The method of claim 4 wherein said delay element is a rigid temperature responsive element which prevents the closing of said port until said rigid element softens, and said rigid element will soften when it is subjected to a temperature of at least 270° F. for at least three minutes.

6. The method of claim 5 wherein the steam applied to said area is at least 97% saturated.

* * * * *